(12) United States Patent
Weidman

(10) Patent No.: US 8,637,590 B2
(45) Date of Patent: Jan. 28, 2014

(54) MARINE ANTIFOULANT COATING

(75) Inventor: Larry Weidman, Overland Park, KS (US)

(73) Assignee: Larry Weidman, Overland Park, KS (US)

( * ) Notice: Subject to any disclaimer, the term of this patent is extended or adjusted under 35 U.S.C. 154(b) by 321 days.

(21) Appl. No.: 12/907,623

(22) Filed: Oct. 19, 2010

(65) Prior Publication Data

US 2012/0094032 A1  Apr. 19, 2012

(51) Int. Cl.
*C09D 5/16* (2006.01)
(52) U.S. Cl.
USPC ......................................... 523/122
(58) Field of Classification Search
USPC .......................................... 524/413; 523/122
See application file for complete search history.

(56) References Cited

U.S. PATENT DOCUMENTS

| | | | |
|---|---|---|---|
| 7,910,648 B2 * | 3/2011 | Weidman | 524/398 |
| 2005/0048218 A1 * | 3/2005 | Weidman | 427/446 |
| 2009/0022899 A1 * | 1/2009 | Weidman | 427/447 |
| 2010/0015349 A1 * | 1/2010 | Weidman | 427/447 |

* cited by examiner

*Primary Examiner* — John Uselding
(74) *Attorney, Agent, or Firm* — Hovey Williams LLP

(57) ABSTRACT

A protective coating applied to the underwater portion of a marine vessel operable to inhibit the growth of marine foulants. The coating comprises a polymer, a marine biocide, a preservative, an antimicrobial agent, and optionally a coloring agent. In certain embodiments, the marine biocide, preservative, and optional antimicrobial agent are chemically bonded with the polymer thereby significantly reducing the ability of the biocide, preservative, and antimicrobial agent to leach from the coating into the surrounding environment.

20 Claims, No Drawings

MARINE ANTIFOULANT COATING

BACKGROUND OF THE INVENTION

1. Field of the Invention

Embodiments of the present invention relate to a coating that is applied to a surface. More particularly, embodiments of the present invention relate to a protective coating that is applied to the underwater portion of a marine vessel so as to inhibit the growth of marine foulants.

2. Description of the Related Art

Marine vessels that reside in a water environment over certain lengths of time can accumulate biological growth, known as foulants, on those surfaces that are in contact with the water. Diverse species of hard and soft fouling organisms, such as barnacles, zebra mussels, algae, and slime, form colonies on the underwater surfaces of the vessel, particularly when a vessel is docked, because each requires a permanent anchorage in order to mature and reproduce. Marine growth fouling adds weight to a ship, increases the amount of fuel consumed, and reduces its speed.

Historically, to combat the growth of marine foulants, the underwater surfaces of ships have been coated with antifoulant paints, which often include toxic materials to inhibit biological growth. The antifoulant paints may degrade and break down over time, releasing the toxic materials from the marine vessel into the surrounding water. These toxic materials may include volatile organic compounds (VOCs) and hazardous air pollutants (HAPs). The International Maritime Organization and the United States Environmental Protection Agency have enacted regulations and standards that restrict the emission of VOCs and HAPs from antifoulant paints. The decomposition and break down of the antifoulant paint results in reduced efficacy of the protection afforded by the antifoulants, thereby requiring reapplication of the paint in a relatively short time. Thus, a coating material is required that can be applied to the underwater surfaces of a marine vessel which repels the growth of fouling organisms on such surfaces and has an extended lifetime without releasing significant amounts of toxic materials into the environment.

SUMMARY OF THE INVENTION

Embodiments of the present invention solve the above-mentioned problems and provide a distinct advance in the art of coatings applied to a surface. More particularly, embodiments of the invention provide a protective coating applied to the underwater portion of a marine vessel operable to inhibit the growth of marine foulants. Furthermore, the coating does not degrade significantly over time which leads to a longer effective lifetime and a greatly reduced emission of toxic materials as compared with conventional antifoulant paints.

Various embodiments of the present invention provide an antifoulant coating comprising a polymer that adheres to a surface of a marine vessel that contacts water, a preservative, a marine biocide, and an antimicrobial agent. In certain embodiments, the preservative, the marine biocide, and the antimicrobial agent are chemically bonded to the polymer so as to prevent leaching of the preservative, the biocide, and/or the antimicrobial agent into the surrounding marine environment.

In another embodiment, a method of forming a marine antifoulant coating is provided. The method comprises mixing together components of the coating including a polymer, a marine biocide, a preservative, and an antimicrobial agent. The coating is heated to a temperature above the glass transition temperature of the polymer such that the polymer has particles of the biocide, the preservative, and the antimicrobial agent dispersed therein. While the coating is still heated to a temperature above the glass transition temperature of the polymer, it passes between first and second electrodes which are spaced apart and have a voltage difference in order to alter the orientation of the polymer and the particles of biocide and preservative relative to each other.

In yet another embodiment, a method of forming and applying a marine antifoulant coating to a surface of a marine vessel is provided. The method comprises mixing together components of the coating including a polymer, a marine biocide, a preservative, and an antimicrobial. The coating is heated to a temperature above the glass transition temperature of the polymer such that the polymer has particles of the biocide and preservative dispersed therein. While the coating is still heated to a temperature above the glass transition temperature of the polymer, it passes between first and second electrodes which are spaced apart and have a voltage difference in order to alter the orientation of the polymer and the particles of biocide and preservative relative to each other. The coating is injected into a plasma stream. The plasma stream and the coating are enshrouded with a shielding gas to prevent contamination of the coating. The plasma stream and the coating are directed onto the marine vessel surface whereby the coating becomes adhered to the surface.

This summary is provided to introduce a selection of concepts in a simplified form that are further described below in the detailed description. This summary is not intended to identify key features or essential features of the claimed subject matter, nor is it intended to be used to limit the scope of the claimed subject matter.

Other aspects and advantages of the present invention will be apparent from the following detailed description of the preferred embodiments.

DETAILED DESCRIPTION OF THE PREFERRED EMBODIMENTS

The embodiments illustrated in the following detailed description are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

The coating is generally operable to inhibit the growth of marine fouling organisms on the underwater portion of a marine vessel by repelling the marine organisms when they contact the coating. In various embodiments, the coating also reduces the ability of fouling organisms to adhere to the coated marine vessel surface. Some growth of organisms on the coating may occur, particularly when the vessel is idle, but the organisms detach and slough off as the vessel begins moving through the water. The coating prevents the fouling organisms from strongly adhering to the marine vessel so that the motion of water across the surface of the coating serves as a rinsing action to clean the surface of any fouling growth. In addition, it is sometimes desired that the coating possess a certain color to match other features of the vessel, to meet government or military guidelines, or to achieve a general aesthetic. As a result, the coating may include a coloring agent. Accordingly, the percentage amounts of the other components may be adjusted to accommodate the coloring agent.

In various embodiments, the coating comprises a polymer, a marine biocide, a preservative, and an antimicrobial agent. In other embodiments, the coating further comprises a coloring agent.

The polymer component serves as a foundation for the antifoulant coating in which the other components of the coating are dispersed. Without desiring to be bound by any particular theory, it is believed that the polymer functions as a matrix to which the other components are chemically bonded. Furthermore, it is believed that the preservative and marine biocide may be covalently bonded to the polymer, although certainly it is within the scope of the invention for these bonds to be of an ionic nature as well.

In any event, the polymer binds the preservative and marine biocide in the coating and helps to retain them against the target surface, such as the hull of a ship. The polymer may be a polyamide including various types of nylon such as nylon 11 or nylon 12, available from Evonik Industries of Parsippany, N.J., or under the name VESTOSINT® by Degussa of Düsseldorf, Germany. The polymer may also be an impact resistant powder coating resin, such as SURLYN®, ABCITE® X45, ABCITE® X60, or ABCITE® X70 by DuPont of Wilmington, Del. In various embodiments, the listed polymers may be polar in nature. Generally, the polymer presents the characteristics of increased adhesion to various substrates (particularly metal), high impact resistance, and high resistance to degradation.

In various embodiments, the polymer may also include a fluoropolymer, such as polytetrafluoroethylene (PTFE), perfluoroalkoxy polymer resin (PFA), polyethylenetetrafluoroethylene (ETFE), or polyvinylidene fluoride (PVDF), or powdered silicone in combination with any of the polymers listed above. It is possible that the listed components are non-polar. These additive components are typically included to decrease the coefficient of friction of the antifoulant coating and would primarily be used in situations where the vessel is faster moving, thereby benefiting from a decreased drag on the ship.

Generally, the polymer is supplied in a powder form having average particle sizes ranging from about 20 microns ($\mu m$) to about 80 $\mu m$. In other embodiments, the polymer may be supplied in a nano-sized form wherein the average particle size is between about 25 nanometers (nm) to about 40 nm.

The polymer typically presents a glass transition temperature that is lower than the melting point of the other components included in the antifoulant coating. Thus, the polymer enters the glass transition phase and bonds with the other components before the other components begin to melt. Thus, the marine biocide and preservative are present as discrete particles dispersed within the polymer matrix. Additionally, the polymer is compatible with the target surface so as to adhere strongly thereto once applied. The glass transition temperature of the polymer may be within the range of about 176° F. to about 248° F.

The marine biocide generally comprises a metal component such as copper or silver. Biocides containing metal components are well known in the art. The biocide may be supplied as copper oxide (also known as cuprous oxide or $Cu_2O$), copper and silver coated hollow micro spheres, or silver and copper-clad mica flake. Copper oxide is widely used and is available in several grades, Red Copper 97, Premium grade Purple 97N, and Lo-Lo Tint 97N. Copper oxide may be supplied by SCM Metal Products, Incorporated of Research Triangle Park, N.C. In various embodiments, the biocide may include PREVENTOL® or PREVENTOL® A5S by Lanxess Corporation of Pittsburgh, Pa. The biocide may also include a fluorinated compound, a fluorinated sulfenamide, or an aromatic fluorinated sulfenamide. The biocide may further comprise tolyfluanid, CAS No. 731-27-1, CAS Name: 1,1-dichloro-N-[(dimethylamino)sulfonyl]-1-fluoro-N-(4-methylphenyl) methanesulfenamide. However, the marine biocide may comprise any single component listed or combinations thereof. The marine biocide may also include other conventional biocide components, preferably in powder form, that can bond with the polymer.

The marine biocide may be supplied in a micro-sized form, wherein the average particle size is from about 40 $\mu m$ to about 60 $\mu m$, or a nano-sized form, wherein the average particle size is from about 25 nm to about 35 nm. As noted above, the biocide can continue to exist as a plurality of discrete particles dispersed within the polymer matrix once formed into the coating composition.

The preservative may comprise captan, also known as MERPAN® from Mana, Incorporated of Raleigh, N.C. The antimicrobial may also include PREVENTOL®, PREVENTOL® A5S, a fluorinated compound, a fluorinated sulfenamide, an aromatic fluorinated sulfenamide, or tolyfluanid.

The preservative is generally included to protect the polymer from degradation and breakdown due to bacterial or fungal growth, and may include a fungicide that utilizes zinc as a component. The preservative may also include an algicide to inhibit the growth algae on the coating. The preservative may further include preservative components that can be supplied in a powder form and can bond with the polymer.

Generally, the preservative may be provided in a micro-sized form, wherein the average particle size is from about 20 $\mu m$ to about 80 $\mu m$, or a nano-sized form, wherein the average particle size is from about 25 nm to about 40 nm.

The antimicrobial agent may include antimicrobials such as AgION™ antimicrobial by Agion of Wakefield, Mass., IRGAGUARD®, IRGAROL®, silver zolite, or silver zolite B-5000 by Ciba of Tarrytown, N.Y., indium oxide or indium-tin oxide by Indium Corporation of Utica, N.Y., and NANOKLEAN™ by Envont Technologies of Chesterfield Township, Mich. The antimicrobial may also include PREVENTOL®, PREVENTOL® A5S, a fluorinated compound, a fluorinated sulfenamide, an aromatic fluorinated sulfenamide, or tolyfluanid. The antimicrobial agent may be included to provide additional protection against microbial growth that could cause staining or degradation of the antifoulant coating or that could lead to the growth of larger organisms. Typically, as the level of the antimicrobial is increased, the level of the preservative is decreased. Thus, there is a tradeoff between additional prevention of foulant growth and preservation of the polymer. The antimicrobial may be added depending on the characteristics of the water in which the vessel is anticipated to reside primarily. Furthermore, the antimicrobial agent is generally provided in a blendable powder form and is capable of bonding with the polymer.

The coloring agent may represent any color or shade and may comprise any pigment, tint, dye, or stain that is available in powder form. The coloring agent may be provided in a nano-sized form, wherein the average particle size is from about 10 nm to about 100 nm. Various embodiments may include carbon black pigment available from Degussa, CAS No. 1333-86-4.

It is possible that one or more of the polymer, the marine biocide, the preservative, and optionally the antimicrobial agent may present a net positive or negative electrical charge in order to aid with bonding of the components. It is also possible that the above components may present polar regions as opposed to a full charge.

In some embodiments, the antifoulant coating comprises from about 25% to about 35% by weight of the polymer, from about 50% to about 65% by weight of the marine biocide, from about 4% to about 10% by weight of the preservative, from about 2% to about 6% by weight of the antimicrobial agent, and when present, from about 0.25% to about 2% by weight of the coloring agent. In other embodiments, the antifoulant coating comprises from about 30% to about 32% by weight of the polymer, from about 56% to about 60% by weight of the marine biocide, from about 6.5% to about 9.5% by weight of the preservative, from about 2.5% to about 4.5% by weight of the antimicrobial agent, and when present, from about 0.5% to about 1% by weight of the coloring agent. Also when present, the additive fluoropolymer or silicone powder is present at a level of from about 10% to about 20% by weight.

The amount of the marine biocide present in the coating may be varied in response to the amount and/or type of marine fouling organisms present in the water in which the marine vessel may travel. In some bodies of water, the volume of fouling organisms may be high or the fouling organisms may be more persistent. In response, the amount of the marine biocide may be increased toward the maximum value of the range presented above. Typically, the amounts of the other components are reduced proportionally to compensate for the increase of the marine biocide.

The components are generally supplied in a powder form with a particle sizes as described above. The polymer, the marine biocide, the preservative, the antimicrobial agent, and optionally the coloring agent and fluoropolymer or silicone powder are mixed in a blender to yield a uniform powder material. The blender may be cooled to prevent overheating and coagulation of the mixture.

In some embodiments, the target surface may be cleaned and any debris may be removed so that the coating is applied directly to the surface, such as a steel hull of a ship. In other embodiments, a primer may be applied to the surface before the coating is applied. The primer may include a single polymer, such as nylon 12, or a polymer blend, such as 50%-50% mixture of ABCITE® X45 and nylon 12. The coating may then be applied on top of the primer.

An exemplary coating is created as follows. The total weight of the coating may be approximately 100 pounds. A first exemplary mixture may include the following components. The polymer component comprises 32 pounds of nylon 12 polymide or VESTOSINT® 2157P that has been precipitated in the form of round-shaped particles, the marine biocide component comprises 57 pounds of cuprous oxide, the preservative component comprises 7 pounds of MERPAN® captan, and the antimicrobial agent comprises 4 pounds of silver zolite.

A second exemplary mixture may include the following components. The polymer component comprises 30 pounds of nylon 12 polymide or VESTOSINT® 2161P that has been precipitated in the form of round-shaped particles, the marine biocide component comprises 58 pounds of cuprous oxide, the preservative component comprises 9 pounds of PREVENTOL® A5S, and the antimicrobial agent comprises 3 pounds of silver zolite.

The above coating components from either mixture are placed in a water jacket-cooled Henschel blender and mixed at 3600 rpm for two minutes. Next, the coating is heated to a temperature sufficient to exceed the glass transition temperature of the polymer, and perhaps even the melting point of the polymer, but not great enough to melt the other components. Generally, the coating is heated to between about 220° F. and about 275° F. Thus, the polymer becomes flowable and can bond with the other components. Generally, the biocide, the preservative, and the antimicrobial agent do not bond with each other, but instead are dispersed within the polymer matrix. In certain embodiments, the components comprising the antifoulant coating form bonds with each other to produce a four-part structure, and in embodiments also comprising a coloring agent, a five-part structure. In each instance, the biocide, the preservative, the antimicrobial agent, and the optional coloring agent bond or interact directly with the polymer as opposed to each other.

While the coating is still between about 220° F. and about 275° F. from the heating step above and has energy to form bonds, the coating may pass through an electric field that is capable of varying in magnitude and direction, in which the components may have their radial velocity adjusted, be separated, reoriented, or otherwise manipulated in order to maximize the percentage of material that forms a four-part (or five-part) bonded structure. Thus, the coating is generally in motion and not yet applied to anything when it is exposed to the electric field. The electric field may be created by a first electrode, or other electrically conductive component, and a second electrode that are spaced apart and opposingly aligned with one another. In various embodiments, the first electrode and the second electrode may both include a plurality of physical electrodes or conductors. Generally, the first electrode is charged to a greater voltage than the second electrode.

The electric field is generally applied to a confined space, such as a chamber through which the material passes, so that the motion of the components may be precisely controlled. Thus, the first electrode and the second electrode may be placed on opposing sides of the chamber such that the coating, while still heated as described above, passes in flight between the first and second electrodes. During operation, the electric field may be applied to the chamber so that the polymer is physically aligned in the proper orientation with the marine biocide, the preservative, the antimicrobial, and optionally the coloring agent, to form the four or five-part bonded structure. The exposure to the electric field may increase the amount of covalent bonding that occurs between the polymer and each of the marine biocide, the preservative, the antimicrobial, and the optional coloring agent.

After being exposed to the electric field, the coating is injected into a plasma stream that is surrounded by a shielding gas to prevent contamination of the coating during transport to the target surface. The temperature of the coating must be maintained at or above the glass transition temperature of the polymer until the coating impacts the target surface (i.e., a portion of the surface of a marine vessel). However, if the coating becomes too warm, the bonds between the polymer and the other components may break thereby leading to the decomposition of the coating. Excessive temperatures may also lead to the formation of bonds between the marine biocide, the preservative, and/or the antimicrobial thereby minimizing the effectiveness of the coating to prevent foulant growth. Further, if the coating cools before impacting the surface, its ability to adhere to the surface may be adversely affected. The coating may not evenly adhere to the surface thereby decreasing the lifetime of the coating.

In various embodiments, the coating may be applied to a primer coating comprising only the polymer if the target surface has some chemical or physical characteristics or possibly contaminants that may affect the adherence of the coating. A polymer primer coat generally increases the adherence of the antifoulant coating to the target surface.

In various embodiments, the coating is applied to a target surface using a high-velocity impact fusion plasma spray gun apparatus, such as the one disclosed in U.S. patent application Ser. No. 11/758,991, filed Jun. 6, 2007, which is herein incorporated by reference. For use with the spray gun apparatus, the coating components may be blended or mixed as discussed above and placed into a bin or hopper that is capable of supplying the coating in a pressurized form to the spray gun apparatus.

The spray gun apparatus may include a heating chamber, an electric field chamber, and a plasma nozzle. Upon being supplied to the spray gun apparatus, the coating may enter the heating chamber, wherein the coating may be heated to around the temperature of the glass transition point of the polymer, which may be between about 220° F. and about 275° F.

While still heated to the same temperature range, the coating may pass from the heating chamber to the electric field chamber, wherein the coating may pass through an electric field that is capable of varying in magnitude and direction. The electric field may be created by first and second electrodes that are positioned on opposite sides of the electric field chamber. The coating may pass between the first and second electrodes, where the other components may be reoriented or adjusted with respect to the polymer in order to increase the amount of covalent bonding that occurs between the polymer and each of the marine biocide, the preservative, the antimicrobial, and the optional coloring agent.

The coating may pass through the electric field chamber and be injected into a plasma stream within the plasma nozzle. The plasma stream may be traveling at a high velocity in order to provide energy for the coating to impact the target surface and stick. The plasma stream may be surrounded by a shielding gas to prevent contamination of the coating during transport to the target surface.

Although the invention has been described with reference to the preferred embodiment illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A marine antifoulant coating for application to a surface of a marine vessel said coating comprising:
   between about 30% to 32% by weight of a polymer;
   between about 50% to about 60% by weight of a marine biocide; and
   between 6.5% to about 9.5% by weight of a preservative that is chemically bonded with said polymer.

2. The coating of claim 1, wherein said coating further comprises between about 2.5% to about 4.5% by weight of an antimicrobial agent.

3. The coating of claim 2, wherein said antimicrobial agent comprises a fluorinated compound.

4. The coating of claim 2, wherein said antimicrobial agent comprises a fluorinated sulfenamide.

5. The coating of claim 2, wherein said antimicrobial agent comprises an aromatic fluorinated sulfenamide.

6. The coating of claim 2, wherein said antimicrobial agent comprises tolyfluanid.

7. The coating of claim 1, wherein said marine biocide comprises cuprous oxide.

8. The coating of claim 1, wherein said marine biocide comprises a fluorinated compound.

9. The coating of claim 1, wherein said marine biocide comprises a fluorinated sulfenamide.

10. The coating of claim 1, wherein said marine biocide comprises an aromatic fluorinated sulfenamide.

11. The coating of claim 1, wherein said marine biocide comprises tolyfluanid.

12. The coating of claim 1, wherein said preservative comprises a fluorinated compound.

13. The coating of claim 1, wherein said preservative comprises a fluorinated sulfenamide.

14. The coating of claim 1, wherein said preservative comprises an aromatic fluorinated sulfenamide.

15. The coating of claim 1, wherein said preservative comprises tolyfluanid.

16. The coating of claim 1, wherein said polymer presents a particle size from about 25 nanometers to about 40 nanometers.

17. The coating of claim 1, wherein said marine biocide presents a particle size from about 25 nanometers to about 35 nanometers.

18. The coating of claim 1, wherein said preservative presents a particle size from about 25 nanometers to about 40 nanometers.

19. The coating of claim 1, wherein said marine biocide and preservative are dispersed within said polymer.

20. The coating of claim 1, wherein said polymer is chemically bonded with said marine biocide.

* * * * *